United States Patent [19]

Lin

[11] 4,211,233
[45] Jul. 8, 1980

[54] URETHRAL CATHETER

[76] Inventor: Edward D. Lin, 3663 Grand Ave., Apt. 706, Des Moines, Iowa 50312

[21] Appl. No.: 867,095

[22] Filed: Jan. 5, 1978

[51] Int. Cl.² ............................................ A61M 25/00
[52] U.S. Cl. ................................. 128/349 B; 128/241
[58] Field of Search ............... 128/240, 241, 265–246, 128/348, 349 B, 349 BV, 350 R, 325

[56] References Cited

U.S. PATENT DOCUMENTS

| 550,238 | 11/1895 | Allen | 128/241 X |
|---|---|---|---|
| 3,046,988 | 7/1962 | Moreau et al. | 128/325 |
| 3,173,418 | 3/1965 | Baran | 128/351 |
| 3,394,705 | 7/1968 | Abramson | 128/349 B |
| 3,593,713 | 7/1971 | Bogoff et al. | 128/349 B X |
| 3,860,007 | 1/1975 | Binard et al. | 128/349 B |
| 3,889,686 | 6/1975 | Duturbure | 128/349 B |

Primary Examiner—Dalton L. Truluck
Attorney, Agent, or Firm—Clarence A. O'Brien; Harvey B. Jacobson

[57] ABSTRACT

An elongated tube is provided defining an internal longitudinal passage therein and having a tip at its forward end. The tube includes two lateral openings formed therein closely proximal the tip opening into the passage and an inflatable body is supported from and encircles the tube proximal the lateral openings. A partially inflatable ring is supported from and encircles the tube closely proximal the body and the ring has outwardly facing openings formed therein at points spaced thereabout. First and second longitudinal passageways extend along the tube independent of the aforementioned passage and open, at their forward ends, into the body and ring, respectively.

11 Claims, 11 Drawing Figures

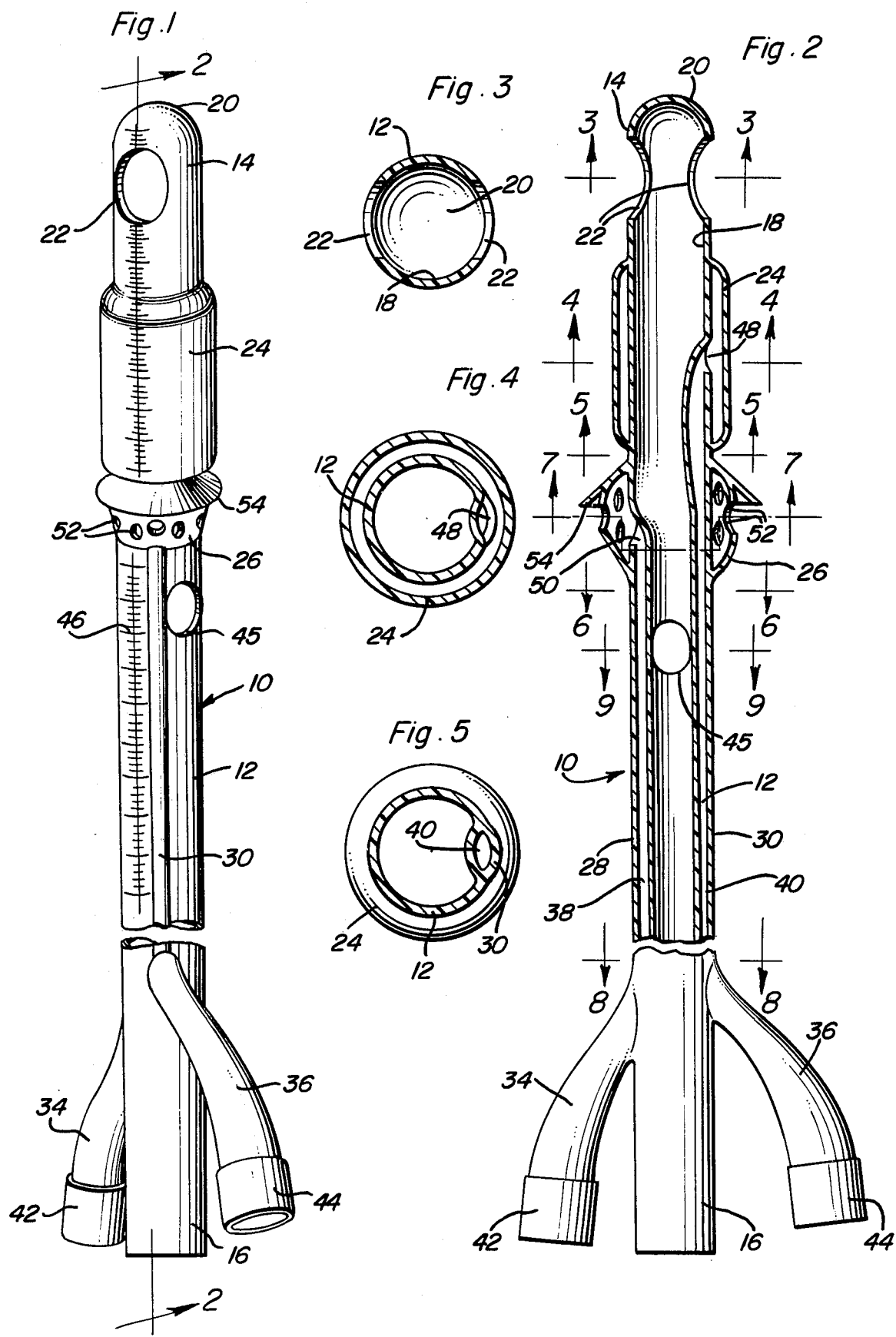

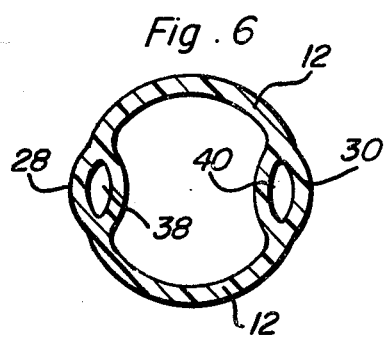
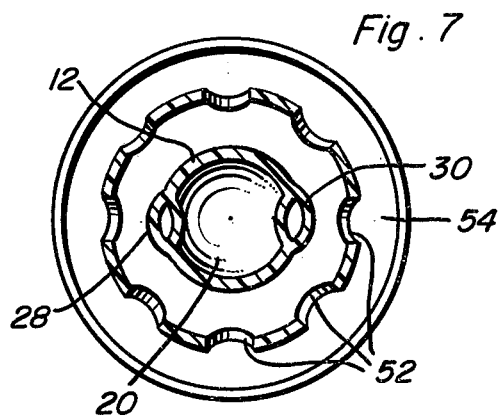
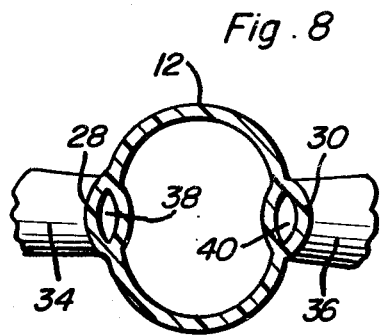
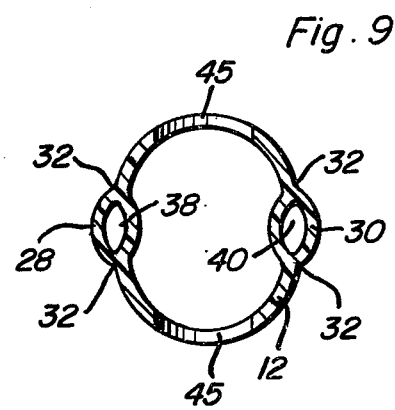
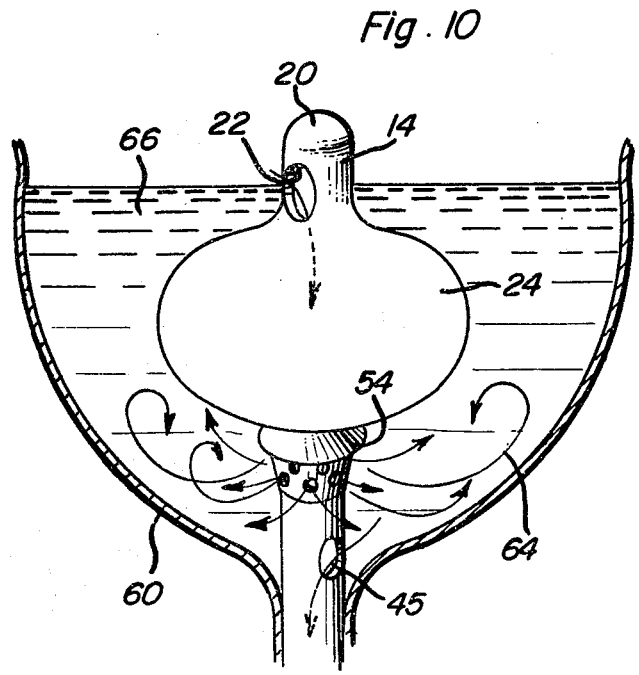
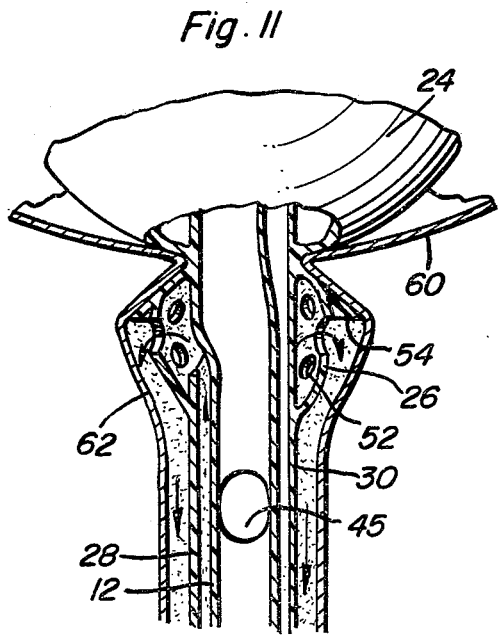

URETHRAL CATHETER

BACKGROUND OF THE INVENTION

Various forms of urethral catheters have been heretofore provided. Many different forms of previously known catheters are designed to perform specific functions and, depending upon the specific functions to be performed, in many instances different catheters must be inserted to perform a series of different functions. Although the insertion and withdrawal of catheters are often uncomfortable or painful and difficult procedures to perform, conventional catheters in common use have no provisions to ease such problems. Most of the lubricant applied to either the urethra of the surface of these catheters before insertion are either pushed ahead of the tip of the catheter as it is inserted or skimmed off by the urethra and remain outside where the lubricant cannot perform its intended function. Further, lubrication to ease withdrawal is not possible with catheters now in common use. The instant invention has special features that enable easy and effective lubrication during both insertion and withdrawal. Further, many catheters designed in a manner to accomplish irrigation of the bladder are not constructed in a manner whereby thorough or continuous irrigation may be accomplished and still further forms of catheters are unable to effectively prevent, to a great degree, ascending urinary tract infections.

Accordingly, a great need exists for a catheter capable of performing numerous functions and which will also be operational to prevent, to a great degree, ascending urinary tract infections.

Various forms of catheters including some of the general structural and operational features of the instant invention are disclosed in U.S. Pat. Nos. 3,394,705, 3,593,713, 3,889,686 and 3,902,492.

BRIEF DESCRIPTION OF THE INVENTION

The catheter of the instant invention includes an elongated tube defining an internal passage therein and having a closure tip at its forward end. The tube includes two lateral openings formed therein closely proximal the tip and opening into the aforementioned passage. An inflatable body is supported from and encircles the tube proximal the lateral openings. A partially inflatable ring is also supported from and encircles the tube closely proximal the inflatable body and the ring has outwardly facing openings formed therein at points spaced thereabout. Further, the tube includes opposite side tubules extending therealong defining first and second longitudinal passageways extending along the tube independent of the main passage and opening at their forward ends, into the interiors of the inflatable body and ring, respectively.

The catheter may be utilized for thorough irrigation of a bladder, outward flushing of the uretha from the juncture between the prostate and the bladder and lubrication of the catheter, closely proximal to the tip thereof, during, and to greatly ease, both insertion and withdrawal of the catheter.

The main object of this invention is to provide a multi-purpose urethral catheter capable of performing multiple functions. without withdrawal thereof.

Another object of this invention is to provide a catheter which may be used to inject lubricant into the associated urethra closely proximal to the tip of the catheter during both insertion and withdrawal of the latter.

Yet another object of this invention is to provide a catheter constructed in a manner facilitating unobstructed drainage of urethral exudate.

A further object of this invention is to provide a cather constructed with scale markings on the external surface that enable simple, rapid and accurate determination of the length of catheter inserted into the urethra or bladder, length of urethra, site of stricture or obstruction, and other measurements.

A still further object of this invention is to provide a catheter capable of thorough and continuous irrigation of the bladder.

Another important object of this invention is to provide a catheter constructed in a manner to facilitate total drainage of an associated bladder.

Still another important object of this invention is to provide a catheter constructed in a manner to enable administering of antibiotics, fungicides and other medications to the urethra closely proximal to the bladder in a manner to prevent, eradicate or eliminate ascending urinary tract infections.

A final object of this invention to be specifically enumerated herein is to provide a catheter in accordance with the preceding objects and which will conform to conventional forms of manufacture, be of simple construction and easy to use so as to provide a device that will be economically feasible, long lasting and relatively trouble-free in operation.

These together with other objects and advantages which will become subsequently apparent reside in the details of construction and operation as more fully hereinafter described and claimed, reference being had to the accompanyings drawings forming a part thereof, wherein like numerals refer to like parts throughout.

BRIEF DESCRIPTION OF THE DRAWINGS

FIG. 1 is an enlarged elevational view of the catheter of the instant invention with a portion of the total length thereof being broken away;

FIG. 2 is a longitudinal sectional view taken substantially upon the plane indicated by the section line 2—2 of FIG. 1;

FIG. 3 is an enlarged transverse sectional view taken substantially upon the plane indicated by the section line 3—3 of FIG. 2;

FIG. 4 is an enlarged transverse view taken substantially upon the plane indicated by the section line 4—4 of FIG. 2;

FIG. 5 is an enlarged transverse sectional view taken substantially upon the plane indicated by the section line 5—5 of FIG. 2;

FIG. 6 is an enlarged transverse sectional view taken substantially upon the plane indicated by the section line 6—6 of FIG. 2;

FIG. 7 is a fragmentary further enlarged transverse sectional view taken substantially upon the plane indicated by the section line 7—7 of FIG. 2;

FIG. 8 is an enlarged transverse sectional view taken substantially upon the plane indicated by the section line 8—8 of FIG. 2;

FIG. 9 is an enlarged transverse sectional view taken substantially upon the plane indicated by the section line 9—9 of FIG. 2;

FIG. 10 is a fragmentary perspective view of the catheter in use for irrigating an associated bladder; and FIG. 11 is a fragmentary enlarged vertical sectional view of the median portion of the catheter in use to administer antibiotics, fungicides, and other medications to the urethra immediately proximal of the bladder.

DETAILED DESCRIPTION OF THE INVENTION

Referring now more specifically to the drawings, the numeral 10 generally designates the catheter of the instant invention. The catheter 10 comprises an elongated tubular member 12 including forward and proximal ends 14 and 16. The tubular member 12 defines an internal longitudinal passage 18 therewithin and the forward end of the tubular member 12 includes a rounded closure tip 20. The forward end portion of the tubular member 12 includes diametrically opposite large diameter lateral openings 22 and the tubular member 12 has an inflatable body or balloon 24 supported therefrom and extending thereabout proximal of the openings 22. Also, the tubular member 12 includes a partially inflatable ring 26 supported therefrom and extending thereabout closely proximal of the body or balloon 24.

The exterior of the tubular member 12 has a pair of diametrically opposite longitudinally extending tubules 28 and 30 supported therefrom and extending therealong and each tubule projects slightly outwardly from the adjacent outer surfaces of the tubular member 12 and defines a pair of shallow grooves 32 extending along the tubular member 12 and angularly displaced thereabout on opposite sides of the corresponding tubule.

The proximal end 16 of th tubular member 12 includes a pair of tube sections 34 and 36 supported therefrom including outlet ends which open into the proximal ends of the passageways 38 and 40 defined by the tubules 28 and 30. The proximal ends of the tube sections 34 and 36 include valved inlet ends 42 and 44, respectively, into which various liquids and air may be introduced.

The tubular member 12 includes diametrically opposite lateral openings 45 proximal to the ring 26 and the centers of the openings 45 are spaced approximately three centimeters or less from the section of the tubular member 12 defined between the body 24 and the ring 26. Further, the exterior of the tubular member 12 has a scale 46 extending therealong by which the penetration of the catheter 10, measured in centimeters, may be accurately determined.

The forward end of the tubule 30, and thus the passage-way 40, opens into the longitudinal midportion of the body 24 as at 48 and the forward end of the tubule 28, and thus the passageway 38, opens into the interior of the ring 26 as at 50.

The ring 26 has circumferentially and longitudinally spaced openings 52 formed therein and the forward end of the ring 26 includes an integral soft skirt 54 of generally truncated cone-shaped configuration.

The body or balloon 24 does not have outlet openings formed therein. Accordingly, air may be introduced into the proximal end of the tube section 36 in order to positively inflate the balloon 24. However, the ring 26 includes the openings 52 and may, therefore, be only partially inflated. However, the ring 26 is partially inflatable either with fluid lubricant or fluid antibiotics, fungicides, and other medications for treating the interior of the urethra proximal to the skirt 54. In addition, other irrigating liquids may be introduced into the passageway 38 for discharging through the openings 52. Such irrigating liquids will then pass rearwardly along the exterior of the catheter 10.

In operation, the catheter 10 is inserted in the usual manner, except that in addition to a small quantity of lubricant expressed into the urethra prior to insertion of the catheter 10 and external lubrication applied to the exterior of the forward end of the catheter 10, lubricant may be introduced into the tube section 34 for discharging from the openings 52 during insertion as well as during withdrawal of the catheter 10. If it is desired to irrigate the associated bladder 60, the catheter 10 may be inserted until the openings 45 are positioned just inwardly of the bladder 60. This operation may be accomplished by first inserting the catheter 10 to a position with the partially inflated ring 26 at the juncture between the urethra 62 and the bladder 60. Inflating the balloon 24 after insertion of catheter into bladder 60 followed by gentle tugging of catheter until resistance is felt, positively signals that this initial position has been reached. Then, the position of the scale 46 at he distal end of the urethra 62 may be noted and the catheter 10 may then be further inserted approximately three centimeters. This will insure that the openings 45 are just within the bladder 60. At this point, bladder irrigating liquids may be introduced into the tube section 34 for irrigating the bladder 60. The irrigating liquids will exit from the openings 52 in the manner indicated by the arrows 64 in FIG. 10 and the liquid 66 within the bladder 60 will drain therefrom through the openings 22 and 45 for complete drainage.

If it is desired to medicate the urethra in order to prevent, eradicate or eliminate ascending urinary tract infections, the ring 26 is allowed to deflate and the ring and skirt 54 are withdrawn from the bladder 60 to the position thereof illustrated in FIG. 11 of the drawings. Thereafter, the antibiotic, fungicide, or other fluent medication may be introduced into the tube section 34 for passage upwardly through the passageway 38 and into the ring 26 whereby the latter will be partially inflated and the fluent material will be discharged from the partially inflated ring 26 through the openings 52 and then passed downwardly along the exterior of the catheter 10 within the urethra. Because of the skirt 54 which defines a circumferentially extending seal structure disposed about the tubular member 12 for sealed engagement with the urethra 62, as irrigating fluids are discharged outwardly from the ring 26 through the openings 52 upward movement of the irrigating fluids past the skirt 54 is prevented and thus the irrigating fluids flow downwardly along the exterior of the tubular member 12 and the tubules 28 and 30 for eradicating or eliminating ascending infections, see FIG. 11.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents, including those for use in other bodily cavities other than urethra and bladder, may be resorted to, falling within the scope of the invention.

What is claimed as new is as follows:

1. A urethral catheter for thorough irrigation of a bladder, outward flushing from prostatic urethra and lubrication closely proximal to the tip during both insertion and withdrawal, said catheter comprising an elongated tube having forward and rearward ends and defining an internal longitudinal passage therein and having a tip at its forward end, said tube including a lateral opening formed therein closely spaced rearward of said tip and opening into said passage, an inflatable body supported from and encircling said tube and spaced rearward therealong from said lateral opening, an axially short partially inflatable ring supported from and encircling said tube and closely spaced along said tube rearward of said body, said ring having outwardly facing openings formed therein at points spaced thereabout, said elongated tube including means defining first and second longitudinal passageways extending therealong independent of said passage and opening, at their forward ends, into said body and ring, respectively, said elongated tube intermediate said ring and said inflatable body, including circumferential seal means extending completely thereabout and projecting outwardly therefrom for preventing upward fluid flow therepast, whereby irrigating fluids discharged from said outwardly facing ring openings will be directed downwardly therefrom for eradicating or eliminating ascending infections.

2. The combination of claim 1 wherein said tube includes a second lateral opening formed therein proximal said ring.

3. The combination of claim 1 wherein said first and second longitudinal passageways are defined by tubules supported from and extending along diametrically opposite sides of said tube on the exterior thereof.

4. The combination of claim 3 wherein the junctures of each of said tubules with said tube, at points angularly spaced thereabout define shallow outwardly opening grooves on the exterior of said tube extending along opposite sides of each of said tubules.

5. The combination of claim 1 wherein said outwardly facing openings also include openings spaced along the length of said ring.

6. The combination of claim 1, including scale means on said tube, said scale means extending longitudinally of said tube and being graduated in centimeters and millimeters.

7. A urethral catheter for thorough irrigation of a bladder, outward flushing from prostatic urethra and lubrication closely proximal to the tip during both insertion and withdrawal, said catheter comprising an elongated tube defining an internal longitudinal passage therein and having a tip at its forward end, said tube including a lateral opening formed therein closely proximal said tip and opening into said passage, an inflatable body supported from and encircling said tube proximal said lateral opening, a partially inflatable ring supported from and encircling said tube closely proximal said body, said ring having outwardly facing openings formed therein at points spaced thereabout, said elongated tube including means defining first and second longitudinal passageways extending therealong independent of said passage and opening, at their forward ends, into said body and ring, respectively, the forward end of said ring includes a soft integral generally truncated cone-shaped skirt whose proximal larger diameter end opens proximally of said ring and projects slightly outwardly beyond the outer surfaces of said ring.

8. The combination of claim 7 wherein said tube includes a second lateral opening formed therein proximal said ring.

9. The combination of claim 8 wherein said first and second longitudinal passageways are defined by tubules supported from and extending along diametrically opposite sides of said tube on the exterior thereof.

10. The combination of claim 9 wherein the junctures of each of said tubules with said tube, at points angularly spaced thereabout define shallow outwardly opening grooves on the exterior of said tube extending along opposite sides of each of said tubules.

11. The combination of claim 10 wherein said outwardly facing openings also include openings spaced along the length of said ring.

* * * * *